(12) United States Patent
Sakaue et al.

(10) Patent No.: US 7,070,948 B1
(45) Date of Patent: Jul. 4, 2006

(54) METHOD FOR ASSAYING GLYCATED PROTEIN

(75) Inventors: Ryoichi Sakaue, Chiba (JP); Ayumi Arai, Chiba (JP); Naoki Kajiyama, Chiba (JP); Yasuji Koyama, Chiba (JP)

(73) Assignee: Kikkoman Corporation, Noda (JP)

( * ) Notice: Subject to any disclaimer, the term of this patent is extended or adjusted under 35 U.S.C. 154(b) by 339 days.

(21) Appl. No.: 10/088,524

(22) PCT Filed: Sep. 29, 2000

(86) PCT No.: PCT/JP00/06808

§ 371 (c)(1),
(2), (4) Date: Apr. 1, 2002

(87) PCT Pub. No.: WO01/25475

PCT Pub. Date: Apr. 12, 2001

(30) Foreign Application Priority Data

Oct. 1, 1999 (JP) ............................. 11-280941

(51) Int. Cl.
*C12Q 1/37* (2006.01)
*C01N 33/53* (2006.01)

(52) U.S. Cl. ............................. 435/23; 435/24; 435/975
(58) Field of Classification Search ............... 435/23, 435/24, 975
See application file for complete search history.

(56) References Cited

U.S. PATENT DOCUMENTS 5,985,591 A * 11/1999 Yonehara et al. ............. 435/28

FOREIGN PATENT DOCUMENTS

| EP | 526150 | 2/1993 |
|---|---|---|
| EP | 598329 | 5/1994 |
| EP | 693559 | 1/1996 |
| EP | 0 921 198 | 6/1999 |
| JP | 9-324732 | * 11/1997 |
| WO | 96/34977 | 11/1996 |
| WO | 97/13872 | 4/1997 |
| WO | 00/50579 | 8/2000 |

OTHER PUBLICATIONS

Uwe Kobold et al.: "Candidate reference methods for hemoglobin $A_{1c}$ based on peptide mapping" Clinical Chemistry, vol. 43, No. 10, pp. 1944–1951.

Nobuyuld Yoshida, et al., "Primary structures of funga fructosyl amino acid oxidases and their application to the measurement of glycated proteins", European Journal of Biochemistry, Berlin, DE, vol. 242, No. 3, Dec. 15, 1996, pp. 499–505.

Sakai, Y. et al, "Purification and Properties of Fructosyl Lysine Oxidase from Fusarium Oxysporum S–1F4", Bioscience Biotechnology Biochemistry, Japan Soc. for Bioscience, Biotechnology and Agrochem. Tokyo, JP, vol. 59, No. 3, Mar. 1995, pp. 487–491.

* cited by examiner

*Primary Examiner*—Louise N. Leary
(74) *Attorney, Agent, or Firm*—Oblon, Spivak, McClelland, Maier & Neustadt, P.C.

(57) ABSTRACT

Based on a principle that is different to that of a conventional enzymatic method, the present invention provides a novel method for assaying a glycated protein by a simple procedure, within a short period of time, and with high accuracy, and a reagent kit for assaying used in the method. The method for assaying a glycated protein in a sample is realized by treating a glycated protein-containing sample with protease to liberate a glycated peptide, preferably an α-glycated peptide, particularly preferably an α-glycated dipeptide, from a glycated protein, allowing an oxidase to react with the liberated glycated peptide, and determining the produced hydrogen peroxide.

28 Claims, 2 Drawing Sheets

METHOD FOR ASSAYING GLYCATED PROTEIN

TECHNICAL FIELD

The present invention relates to a method for assaying a glycated protein in a sample and a reagent kit for assaying, which is used in the assay method.

BACKGROUND ART

A glycated protein is a protein that has been glycosylated in a nonenzymatic manner and produced as a result of nonenzymatic covalent binding between an aldehyde group on a saccharide, i.e., an aldose (a monosaccharide potentially having an aldehyde group or a derivative thereof), and an amino group on the protein. These glycated proteins are also referred to as so-called "Amadori compounds" since they are formed through Amadori rearrangement of a Schiff's base produced as a reaction intermediate.

Glycated protein is contained in biological samples including hair and body fluid such as blood in an organism. The concentration of glycated protein that is present in blood strongly depends on the concentration of saccharides such as glucose dissolved in blood serum. With a diabetic condition, production of glycated protein is accelerated and the concentration of glycated hemoglobin contained in erythrocyte or the concentration of glycated albumin in blood serum reflect the average blood glucose level of the specific past period. Thus, the assay of those glycated proteins is important in diagnosis or control of diabetic symptoms.

Conventional methods known as methods for quantitatively analyzing a glycated protein include a method utilizing high performance liquid chromatography (Chromatogr. sci., 10, 659 (1979)), a method utilizing a column in which a solid prepared by binding a boric acid is packed (Clin. Chem., 28, 2088–2094 (1982)), a method utilizing electrophoresis (Clin. Chem., 26, 1598–1602 (1980)), a method utilizing an antigen-antibody reaction (JJCLA, 18,620 (1993)), a method for performing colorimetric measurement of reducibility using tetrazolium salt (Clin. Chim. Acta, 127, 87–95 (1982)), and a method for performing colorimetric measurement after oxidation with thiobarbituric acid (Clin. Chem. Acta, 112, 197–204 (1981)). An enzymatic method is currently proposed as a method for assaying a glycated protein in which the procedure is carried out in a simpler and more cost-effective manner within a shorter period of time with higher accuracy compared to the above-described methods (Japanese Patent Publication (kokoku) No. 33997/1993 (Hei5-33997), Japanese Patent Laid-Open No. 127895/1999 (Hei11-127895), and WO 97/13872).

In these enzymatic methods, a glycated protein is decomposed with protease and a fructosyl amino acid oxidase is allowed to act on a liberated glycated amino acid to assay the produced hydrogen peroxide. Examples of oxidases disclosed as usable in the enzymatic assay methods include an oxidase produced from a bacteria belonging to the genus *Corynebacterium* (Japanese Patent Publication (kokoku) Nos. 33997/1993 (Hei5-33997) and 65300/1994 (Hei6-65300)), oxidase produced from a fungus belonging to the genus *Aspergillus* (Japanese Patent Laid-Open No. 155780/1991 (Hei3-155780)), an oxidation produced from a fungus belonging to the genus *Gibberella* (Japanese Patent Laid-Open No. 289253/1995 (Hei7-289253)), an oxidase produced from a fungus belonging to the genus *Fusarium* (Japanese Patent Laid-Open Nos. 289253/1995 (Hei7-289253) and 154672/1996 (Hei8-154672)), an oxidase produced from a fungus belonging to the genus *Penicillium* (Japanese Patent Laid-Open No. 336386/1996 (Hei8-336386)), and a ketoamine oxidase (Japanese Patent Laid-Open No. 192193/1993 (Hei5-192193)). These enzymes effectively react with a glycated amino acid. However, the above enzymes do not react with a glycated peptide in which an amino group of a peptide has been glycated.

At present, various glycated proteins are used as an index for diagnosing diabetes. Examples of such glycated proteins include those in which an $\epsilon$-amino group of an internal lysine residue in a protein is glycated (for example, glycated albumin) and those in which an $\alpha$-amino group of an amino acid at the amino terminus of the protein is glycated (for example, glycated hemoglobin (HbAlc)). Currently, however, some glycated proteins cannot be decomposed to quantitatively liberate a glycated amino acid even with the use of conventional protease. In addition, the above-described fructosyl amino acid oxidase, which is currently employed, has a high reactivity to a liberated glycated amino acid although it does not substantially react with a glycated peptide. Thus, the above enzymatic method is not always accurate.

For example, glycated hemoglobin (HbAlc) is produced by glycating an $\alpha$-amino group of an amino acid at the amino terminus of hemoglobin $\beta$-subunit. However, even though various proteases react with the glycated protein, the $\alpha$-glycated amino acid (an $\alpha$-amino group of the amino acid is glycated) cannot be liberated. Thus, even with the use of the above-described fructosyl amino acid oxidase, glycated hemoglobin (HbAlc) cannot be assayed.

At present, methods proposed for assaying glycated hemoglobin (HbAlc) include a method in which glycated hemoglobin is directly assayed in that state by electrosprayionization mass spectrometry (Clinical Test, 42, 304–343 (1997)), a method in which endoproteinase Glu-C is allowed to act on glycated hemoglobin, a liberated $\alpha$-glycated hexapeptide derived from $\beta$-subunit ($\alpha$-amino group of an amino acid at the amino terminus of hexapeptide is glycated) is fractionated by reversed phase high performance liquid chromatography, and the content thereof is determined through mass spectrometry analysis to assay (Clin. Chem., 43, 1944–1951 (1997)), and the like. However, a highly sensitive and expensive assay device is necessary for these methods, and the operation of the assay is complicated, costly, and time-consuming.

The object of the present invention is to overcome the drawbacks of the conventional methods for assaying a glycated protein and to provide a novel method for assaying a glycated protein by a simple procedure based on a principle different from that of the conventional enzymatic methods in a cost-effective manner within a short period of time with high accuracy.

DISCLOSURE OF THE INVENTION

We have conducted concentrated studies to attain the above object and as a result have found that, by a certain type of protease treatment, an $\alpha$-glycated peptide having a specific number of amino acid residues (a glycated peptide in which an $\alpha$-amino group of an amino acid at the amino terminus of the peptide has been glycated), particularly an $\alpha$-glycated dipeptide (a glycated dipeptide in which an $\alpha$-amino group of an amino acid at the amino terminus of the dipeptide has been glycated), is efficiently liberated from a glycated protein and that an enzyme in which a fructosyl amino acid oxidase produced from microorganisms is modified acts on the liberated $\alpha$-glycated peptide, especially an α-glycated dipeptide in a specific manner, to produce hydrogen peroxide. Further, an α-glycated peptide liberated from the glycated protein can be assayed by HPLC or using the above-described oxidase, and as a result, a glycated protein can be assayed by a simple procedure, within a short period of time, and with high accuracy. This has led to the completion of the present invention.

The present invention provides a method for assaying the presence and/or amount of a glycated protein in a sample, and a reagent kit for assaying, which is used in the above method. In the assay method, a sample containing or capable of containing a glycated protein is treated with protease, and when a glycated protein is present, a glycated peptide, preferably an α-glycated peptide, particularly preferably an α-glycated dipeptide, is liberated therefrom, and an oxidase having an activity to produce hydrogen peroxide upon reacting with the glycated peptide is allowed to act on those liberated glycated peptides, thereby assaying the resultant hydrogen peroxide and the like, or alternatively, the liberated glycated peptide is assayed by HPLC.

Another aspect of the present invention provides a method for assaying the presence and/or amount of a glycated peptide in a sample by allowing an oxidase having an activity to produce hydrogen peroxide upon reacting with a glycated peptide to react with a sample containing or capable of containing the glycated peptide to assay the resulting hydrogen peroxide and the like.

More specifically, the present invention provides the following (1) to (12).

(1) A method for assaying the presence and/or amount of a glycated protein in a sample, wherein the sample is treated with protease, followed by treatment with an oxidase having an activity to produce hydrogen peroxide upon reacting with a glycated peptide to assay the presence and/or amount of a generated product or consumed substance by the reaction.

(2) The method for assaying the presence and/or amount of a glycated protein according to (1) above, wherein the protease is at least one protease selected from proteases produced by microorganisms belonging to the genus *Aspergillus, Saccharomyces,* or *Bacillus.*

(3) The method for assaying the presence and/or amount of a glycated protein according to (1) above, wherein the glycated peptide is an α-glycated peptide.

(4) The method for assaying the presence and/or amount of a glycated protein according to (3) above, wherein a peptide portion of the α-glycated peptide is a short chain peptide having 2 to 6 amino acids.

(5) The method for assaying the presence and/or amount of a glycated protein according to (3) above, wherein the α-glycated peptide is fructosyl valyl histidine.

(6) The method for assaying the presence and/or amount of a glycated protein according to (1) above, wherein the product to be assayed is hydrogen peroxide.

(7) A method for assaying the presence and/or amount of a glycated protein in a sample, wherein the sample is treated with protease, and the presence or absence, and/or amount of liberation of fructosyl valyl histidine is then assayed by HPLC.

(8) A method for assaying the presence and/or amount of a glycated peptide in a sample, wherein the sample is treated with an oxidase having an activity to produce hydrogen peroxide upon reading with the glycated peptide to assay the presence and/or amount of a generated product or consumed substance produced by the reaction.

(9) A reagent kit for assaying a glycated protein in a sample, comprising the following components:
 (i) protease;
 (ii) an oxidase having an activity to produce hydrogen peroxide by reacting with a glycated peptide; and
 (iii) a reagent for assaying hydrogen peroxide.

(10) The reaction kit for assaying a glycated protein in a sample according to (9) above, wherein the glycated peptide is an α-glycated peptide.

(11) The reagent kit for assaying a glycated protein in a sample according to (10) above, wherein a peptide portion of the α-glycated peptide is a short chain peptide having 2 to 6 amino acids.

(12) The reagent kit for assaying a glycated protein in a sample according to (10) above, wherein the α-glycerated peptide is fructosyl valyl histidine.

This specification includes part or all of the contents disclosed in the specification and/or drawings of Japanese Patent Application No. 280,914/1999 (Hei11-280941), which is a priority document of the present application.

BEST MODE FOR CARRYING OUT THE INVENTION

Figure 1:
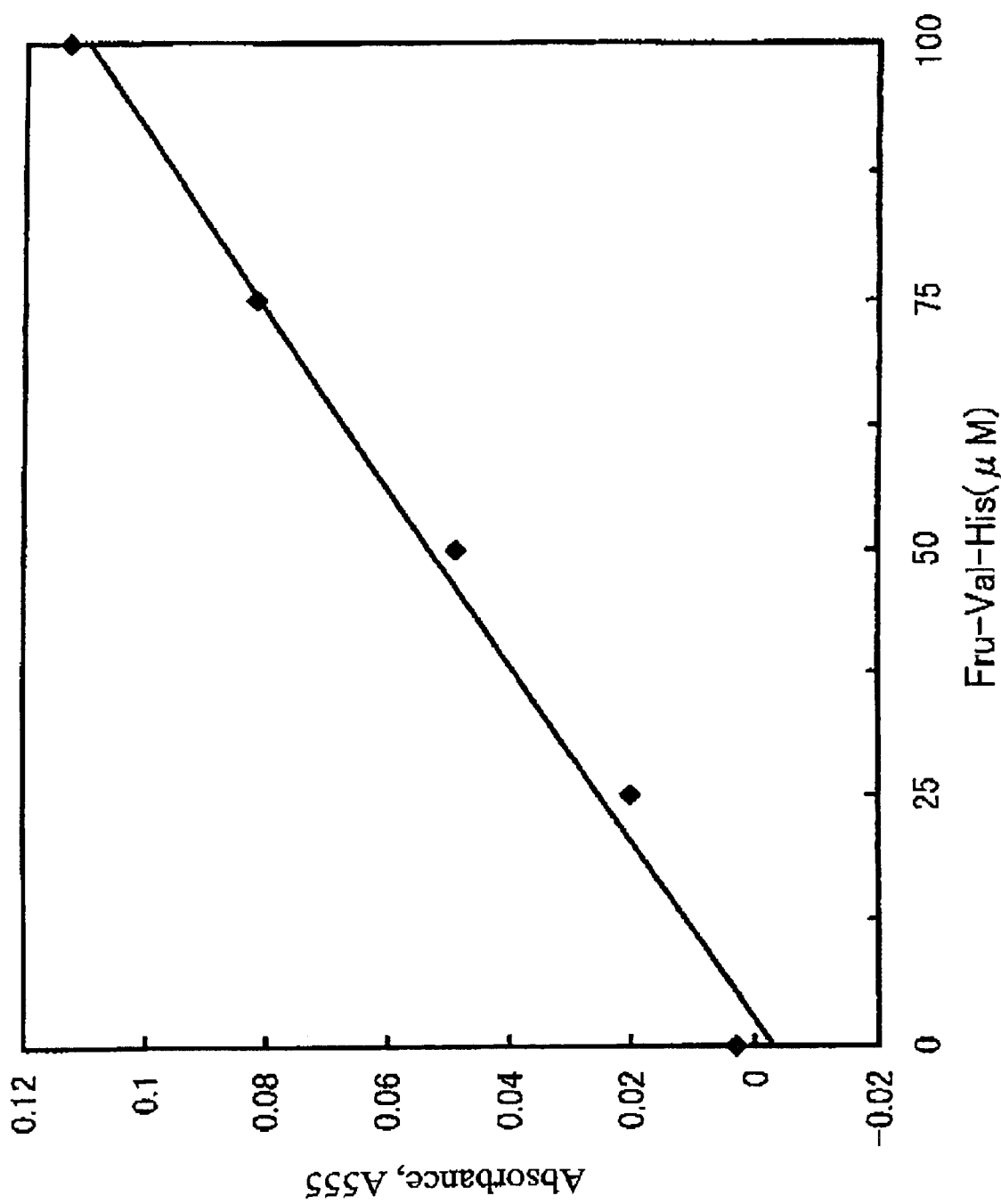
FIG. 1 shows a result of assay of an α-glycated dipeptide (fructosyl valyl histidine) in a sample using a method of the present invention.

The present invention will now be described in detail. As described above, the glycated protein according to the present invention may be of any type so long as it is produced through nonenzymatic binding between a protein and aldose such as glucose. For example, organism-derived glycated protein includes glycated albumin and glycated hemoglobin (HbAlc) and the present invention is preferably used in the assay of, for example, glycated hemoglobin (HbAlc). Further, glycated protein is included in foods at large, for example, juice, candies, seasonings, and powdery foods. Any sample can be utilized as a sample containing the glycated protein of the present invention so long as the glycated protein described above is contained. Examples include hair and body fluids such as blood and saliva in an organism as well as the above-described foods. These samples may be subjected to assay as they are or after filtration, dialysis or the like. Further, for example, the glycated protein to be assayed may be adequately concentrated, extracted, or diluted with water, a buffer or the like.

In the present invention, protease is first utilized to liberate a glycated peptide from a glycated protein. "Protease" as used herein refers to an enzyme having a general protease activity and/or a peptidase activity. Any enzyme may be used as protease so long as the enzyme can react with the glycated protein to liberate the glycated peptide, and suitable enzymes can be appropriately selected depending on the type of the subject glycated protein. Suitable enzymes include, for example, protease and peptidase such as proteinase K, pronase E, thermolysin, subtilisin, carboxypeptidase B, cathepsin, carboxypeptidase, endoproteinase Glu-C, papain, and aminopeptidase. In the present invention, protease capable of efficiently liberating a glycated peptide on which the oxidase used in the present invention, described below, can easily act is desirable. Particularly preferably, protease for efficiently liberating an α-glycated dipeptide includes protease derived from a fungus belonging to the genus *Aspergillus,* for example, "Molsin", "AO Protease", or "Peptidase" (commercially available from Seishin Corporation), carboxypeptidase Y derived from a yeast belonging to the genus *Saccharomyces,* and protease derived from a bacteria belonging to the genus *Bacillus,* such as Protin-P (commercially available from Daiwa Kasei). The above proteases can be used alone or in a combination of two or more.

Any combinations may be employed for treating a sample so long as the protease acts on the glycated protein to be assayed to efficiently liberate the glycated peptide within a short period of time. A amount of protease to be used is appropriately determined depending on the content, treatment conditions and the like of a glycated protein contained in the sample. As one example, 0.5 to 50 mg/mL, preferably 1 to 20 mg/mL, of protease derived from a fungus belonging to the genus *Aspergillus* (for example, Molsin, commercially available from Seishin Corporation) is added. Other protease may be appropriately added as required. When treating with protease, pH may be left unadjusted; however, in order to render the pH value to be suitable for the activity of the protease to be used, pH may be adjusted to 2 to 9, preferably 3 to 8, with the aid of an adequate pH adjuster, for example, hydrochloric acid, acetic acid, sulfuric acid, sodium hydroxide, or potassium hydroxide. A treatment temperature may be, for example, 20 to 50° C., and it may be in a higher temperature range of 45 to 70° C. depending on the type of enzyme to be used. A treatment time may be of any duration so long as it is long enough to decompose a glycated protein, and may be 1 to 180 minutes, preferably 2 to 60 minutes. The resulting reaction mixture may be used as is or appropriately heated, centrifuged, concentrated, diluted or the like, if necessary.

The liberated glycated peptide of the present invention, which is prepared through protease treatment of a sample, includes any type of glycated peptide so long as it is a glycated peptide that can be obtained by treating a glycated protein with the protease and that the oxidase used in the present invention, described below, can easily act thereon, with an α-glycated peptide being preferred, for example, a short chain α-glycated peptide having 2 to 6 amino acids of the peptide or the like. An α-glycated dipeptide, for example, fructosyl valyl histidine (hereinafter abbreviated to "fructosyl Val-His" or "Fru-Val-His") or the like is particularly preferred. Organisms or foods include, for example, a liberated glycated peptide prepared through decomposition of a glycated protein in an organism or in the production process of foods, respectively, and a glycated peptide prepared by binding between a liberated peptide through decomposition of a protein and a saccharide and the like. These are also included in the liberated glycated peptide of the present invention.

Subsequently, the glycated peptide is assayed. Any method can be employed in the present invention as long as the glycated protein can be assayed. Preferred methods for assaying a glycated peptide by a simple procedure, in a cost-effective manner, within a short period of time, and with high accuracy include, for example, a method in which an oxidase is allowed to act and a method in which HPLC is utilized.

A method for causing the oxidase to act of the present invention will now be described. The oxidase is allowed to act on the glycated peptide, and by assaying a generated product or consumed substance by the reaction, the glycated peptide is assayed in an enzymatic manner. Any enzyme can be employed as the oxidase used in the present invention so long as the enzyme (hereinafter referred to as "the oxidase of the present invention") can act in a specific manner on a glycated peptide, preferably an α-glycated peptide, particularly preferably a short chain α-glycated peptide such as an α-glycated dipeptide, to catalyze a reaction for generating hydrogen peroxide. For example, a novel oxidase such as a glycated peptide oxidase can be used.

In general, a microorganism for producing the oxidase of the present invention can be obtained by screening the natural world or the enzyme of the present invention can be obtained by searching from animals or plants. In addition, those prepared through gene recombination of enzymes obtained by searching can be suitably used. Meanwhile, a conventional fructosyl amino acid oxidase may be modified to obtain the oxidase of the present invention. Examples of the conventional fructosyl amino acid oxidase include the oxidase product from a bacteria belonging to the genus *Corynebacterium* (Japanese Patent Publication (kokoku) Nos. 33997/1993 (Hei5-33997) and 65300/1994 (Hei6-65300)), the oxidase produced from a fungus belonging to the genus *Aspergillus* (Japanese Patent Laid-Open No. 155780/1991 (Hei3-155780)), the oxidase produced from a fungus belonging to the genus *Gibberella* (Japanese Patent Laid-Open No. 289253/1995 (Hei7-289253)), the oxidase produced from a fungus belonging to the genus *Fusarium* (Japanese Patent Laid Open Nos. 289253/1995 (Hei7-289253) and 154672/1996 (Hei8-154672)), the oxidase produced from a fungus belonging to the genus *Penicillium* (Japanese Patent Laid-Open No. 336386/1996 (Hei8-336386)), and the ketoamine oxidase (Japanese Patent Laid-Open No. 192193/1993 (Hei5-192193)).

In order to obtain the oxidase of the present invention through modification of the conventional fructosyl amino acid oxidase and the like, a microorganism capable of producing the conventional fructosyl amino acid oxidase and the like is irradiated with ultraviolet ray, X-ray, radiation or the like or is contacted with a mutagen such as ethyl methane sulfonate, N-methyl-N'-nitro-N-nitrosoguanidine, or nitrous acid to perform mutation. The microorganism for producing the oxidase of the present invention is selected from the resulting mutated microorganisms.

In general, however, the oxidase of the present invention can be prepared through introduction of mutation into genes of the conventional fructosyl amino acid oxidase or the like (hereinafter referred to as wild-type genes). Any wild-type genes may be used for introduction of mutation so long as the gene is a wild-type gene of the fructosyl amino acid oxidase or an analogous oxidase and can produce the oxidase of the present invention through introduction of mutation.

The above wild-type gene can be obtained by cloning naturally-occurring genes derived from organisms capable of producing a fructosyl amino acid oxidase, an analogous oxidase or the like, preferably naturally-occurring genes derived from miocroorganisms. Cloning is carried out by first extracting chromosome DNA or mRNA from organisms producing the oxidase in accordance with a conventional method, for example, a method described in Current Protocols in Molecular Biology (WILEY Interscience, 1989). Further, mRNA can be used as a template to synthesize cDNA. A library of the thus obtained chromosome DNA or cDNA is produced. Subsequently, suitable probe DNA is synthesized based on the amino acid sequence of the oxidase and the like to screen the library of DNA or cDNA using the probe DNA. Alternatively, suitable primer DNAs are prepared based on the amino acid sequence of the peptide, DNA containing the subject gene fragment is amplified by a suitable polymerase chain reactor (PCR) such as a 5'RACE or 3'RACE method, and the amplified DNAs are linked to each other to obtain a DNA containing a full length of wild-type gene. As a further example, a method exists in which isolation is carried out in accordance with a conventional method from *Escherichia coli* DH5a (pFA5) (FERM BP-6182) that maintains plasmid DNA coding for a wild-type gene of the present invention derived from a bacteria belonging to the genus *Corynebacterium*, as a generally available source for genes.

Methods for introducing mutation into the wild-type genes include a method in which a wild-type gene is contacted with a mutating agent, for example, an alkylating agent such as nitrosoguanidine, an acridine dye, hydroxylamine, nitrous acid, sulfurous acid, 5-bromouracil, or benzopyrene. In addition, a method for introducing mutation utilizing, for example, ultraviolet radiation, transposon, a cassette-type mutation, chimera gene preparation, PCR, or DNA shuffling can be extensively employed. The wild-type genes for introducing mutation may be genes that were inserted into suitable vector DNA, i.e., recombinant DNA. In this case, recombinant DNA after mutation is purified by ethanol precipitation and the like. The resulting mutated genes can be expressed by genetic transformation or genetic transduction of a host cell utilizing the recombinant DNA. The strain for producing the oxidase of the present invention is selected from a large number of strains maintaining mutated genes.

A method for selecting the subject microorganisms or strains include a method utilizing, as a substrate, an α-glycated peptide, preferably a short chain α-peptide such as an α-glycated dipeptide, an α-glycated tripeptide, or an α-glycated tetrapeptide. An example thereof includes a method utilizing fructosyl Val-His or the like as an α-glycated dipeptide. To the reaction solution containing this substrate is added an enzyme extract prepared by fragmentation or bacteriolysis of bacterial cells of microorganisms or strains to be assayed, or an enzyme extract prepared from the supernatant thereof separated by centrifugation to conduct reaction. The resulting hydrogen peroxide is colored with a commonly employed coloring substrate for hydrogen peroxide described below, thereby selecting the microorganisms or strains for producing the oxidase of the present invention. The enzyme extract may be used in that state, or may be optionally concentrated or diluted. The amount of oxygen decrease due to the enzyme reaction can be measured with an oxidation electrode. In selection, an enzyme reaction may be carried out in a test tube. Examples which may be appropriately adopted include a method in which the reaction is performed in a 96-well microplate, a method in which the reaction is performed by coating or permeating a reaction reagent on a membrane onto which an enzyme extract has been adsorbed, and a method in which the reaction is performed by superimposing a membrane having a reaction reagent coated thereon on a membrane having an enzyme extract adsorbed thereon. Alternatively, selection can be carried out in an efficient simple manner by mixing a plurality of strains to perform several steps of selection.

As described above, *Escherichia coli* (*E. coli*) DH5α (pFP1) can be specifically exemplified as a strain for producing the oxidase of the present invention, which was prepared by modifying a conventional fructosyl amino acid oxidase produced from a bacteria belonging to the genus *Corynebacterium* (Japanese Patent Publication (kokoku) Nos. 33997/1993 (Hei5-33997) and 65300/1994 (Hei6-65300)). *Escherichia coli* (*E. coli*) DH5α(pFP1) was deposited at the RESEARCH INSTITUTE OF BIOSCIENCE AND HUMAN-TECHNOLOGY (1-1-3, Higashi, Tsukuba, Ibaraki, Japan) as of Sep. 22, 1999 under the accession number FERM BP-7297.

The oxidase of the present invention is obtained from tissues of animals, plants and the like containing the enzyme or the microorganisms producing the enzyme by, for example, a conventional extraction method. For example, the oxidase of the present invention is produced using microorganism producing the oxidase of the present invention in the manner described below. The microorganism may be cultured in accordance with a conventional solid culturing technique. Preferably, however, they are cultured in accordance with a liquid culturing technique as much as practically possible. Any medium can be used in culturing as long as a carbon source, a nitrogen source, an inorganic substance, and other nutritive sources are adequately contained therein. The medium may be either synthetic or naturally-occurring, and as long as the medium can be efficiently produced the subject enzyme, any medium may be used. An assimilable carbon compound suffices for the carbon source and examples thereof include glucose, starch hydrolysate, glycerin, fructose, and molasses. Any usable nitrogen compound suffices for a nitrogen source and examples thereof include a yeast extract, a peptone, a meat extract, corn steep liquor, soybean flour, a Malt extract, an amino acid, ammonium sulfate, and ammonium nitrate. Inorganic substances include, for example, various salts such as a common salt, potassium chloride, magnesium sulfate, manganese chloride, iron (I) sulfate, potassium (I) phosphate, potassium (II) phosphate, sodium carbonate, and calcium chloride. In addition, vitamins, antifoaming agents and the like may be optionally added. A substrate on which the oxidase of the present invention acts or an analogous material thereof, for example, glycated peptides, fructosyl amino acid, partial decomposition product of a glycated protein, glycated hemoglobin, glycated albumin, glycated peptide that was artificially glycated through coheating with saccharide, or a glycated protein may be added to increase the amount of the subject enzyme produced. These nutritive sources and substances to be added may be used alone or in combination. Culture conditions vary depending on microorganisms to be cultured. For example, culturing is carried out with the initial pH of the medium being adjusted to 5 to 10, at the culturing temperature of 20 to 40° C., for the culturing time of 10 to 50 hours, preferably 15 to 25 hours, by means of submerged culturing with aerating stirring, shake culturing, stationary culturing or the like.

After the completion of culturing, a conventional means for collecting an enzyme can be employed in order to collect the oxidase of the present invention from the culture product. When the enzyme is present in the strain, preferably, a strain is separated from the cultured product through an operation such as filtration and centrifugation to collect the enzyme from the strain. For example, a method for cleaving strains using a conventional cleavage means such as an ultrasonic crusher, a French press, a DYNO-Mill, a method for dissolving a cell wall of a strain using a cell wall lytic enzyme such as lysozyme, or a method for extracting an enzyme from the strain using a surfactant such as Triton X-100 may be adopted by itself or in combination. Subsequently, an insoluble substance is removed by filtration or centrifugation to obtain an enzyme extract. In order to optionally isolate and purify the oxidase of the present invention from the resultant extract, a nucleic acid is removed therefrom with the aid of streptomycin sulfate, protamine sulfate, manganese sulfate or the like, and ammonium sulfate, alcohol, acetone or the like is then added thereto. The mixture is fractionated and a precipitate is collected, thereby obtaining a crude enzyme. In order to obtain a more purified enzyme sample, for example, gel filtration utilizing Sephadex, ultragel, or biological, an adsorption-elution method utilizing an ion exchanger, hydroxyapatite or the like, affinity chromatography, or fractionation utilizing a molecular sieve membrane, hollow fiber membrane or the like are appropriately selected or performed in combination to obtain an enzyme sample having a desired level of purity. When the enzyme is present outside the strain, in accordance with a conventional method, a culture solution is collected and concentrated after the separating operation of the strain to subject the culture solution to the above various purifying methods.

A titer of the oxidase of the present invention can be measured by, for example, the following method. It can also be measured by other methods and the measuring method is not limited to that described below.

(1) Preparation of Reagents

Regent 1 (R1): 1.0 kU of peroxidase (TYPE III, Toyobo Co.) and 100 mg of 4-aminoantipyrine (TOKYO KASEI KOGYO CO., LTD.) are dissolved in 0.1 M potassium phosphate buffer (pH 8.0) to fix the solution at a constant volume of 1 L.

Reagent 2 (R2): 500 mg of TOOS (N-ethyl-N-(2-hydroxy-3-sulfopropyl)-m-toluidine, DOJINDO LABORATORIES) is dissolved in ion-exchange water to fix the solution at a constant volume of 100 mL.

Reagent (3) (R3): 1.25 g of fructosyl Val-His (MW416, a product process thereof is described below) is dissolved in ion-exchange water to fix the solution at a constant volume of 10 mL.

(2) Assay

100 µL of R2 is added to 2.7 mL of R1, and 100 µL of an enzyme solution containing the oxidase of the present invention is added thereto, followed by mixing. The mixture is preheated at 37° C. for 5 minutes. 100 µL of R3 is then added and the mixture is thoroughly mixed. Thereafter, a spectrophotometer (U-2000A, Hitachi) is used to measure changes in absorbance at 555 nm during the reaction at 37° C. for 5 minutes. A control liquid is prepared according to the same procedure as above except for the addition of 100 µL of ion-exchange water instead of 100 µL of R3. A previously prepared standard solution of hydrogen peroxide is used to provide a graph showing a correlation between the amount of hydrogen peroxide and the amount of a resulting dye (absorbance), from which the amount of hydrogen peroxide corresponding to the change in absorbance is determined. From the obtained value, an activity unit in the enzyme solution is determined. The amount of enzyme that produces 1 µmol of hydrogen peroxide per one minute is determined as 1 U.

The thus-obtained oxidase of the present invention acts on a glycated peptide in a specific manner and has a property that produces hydrogen peroxide. Thus, not only can the oxidase of the present invention enzymatically assay the glycated peptide contained in an organism, food or the like, but it can also enzymatically assay the liberated glycated peptide prepared by treating glycated protein in an organism with protease. Therefore, it is suitable for use as a reagent for assaying the glycated protein of the present invention.

The glycated peptide liberated through protease treatment is acted on by the oxidase of the present invention. The oxidase of the present invention used may be added, amount for example, to bring the final concentration of the reaction mixture to 0.1 to 50 U/mL, preferably 1 to 10 U/mL, although it depends on the amount of the glycated peptide in the mixture. When reacting, the range of pH value is, for example, preferably 3 to 11, particularly preferably 5 to 9. It is preferable to adjust the pH value with the aid of a buffer to be suitable for the assay of the present invention considering the optimal pH value of the oxidase of the present invention, although the pH value is not limited to the optimal value so long as it is a pH that is capable of reacting. The methods for adjusting pH are not particularly limited, and examples of buffers include N-[tris(hydroxymethyl))methyl]glycine, phosphate, acetate, carbonate, tris(hydroxymethyl)-aminomethane, borate, citrate, dimethylglutamate, Tricine, and HEPES. If necessary, the pH value of the reaction mixture after protease treatment is appropriately adjusted to the above pH using a buffer. The reaction time is, for example, 1 to 120 minutes, preferably 1 to 30 minutes, although it depends on the amount of the glycated peptide used as a substrate, and the reaction time may be of any duration so long as it is long enough for the oxidase of the present invention to react with the peptides. The reaction temperature is, for example, 20 to 45° C., and the temperature to be employed in a conventional enzyme reaction can be appropriately selected.

According to the present invention, the oxidase of the present invention acts on the liberated glycated peptide, and by assaying the generated product or consumed substance by the reaction, the glycated peptide is assayed. Substances (products) produced from the glycol peptide by the reaction of the oxidase of the present invention include, for example, peptides, hydrogen peroxide, and glucosone. On the other hand, substances to be consumed (consumed substances) include oxygen molecules. These products and consumed substances can be assayed using respective measuring methods. For example, methods for assaying oxygen molecules include an electrical method using an oxygen electrode and methods for assaying peptides include the assay by separation utilizing a reversed-phase HPLC. Preferably, examples of methods that enable assaying within a short period of time by a simple procedure include a method for assaying hydrogen peroxide.

Hydrogen peroxide produced by the reaction of the oxidase of the present invention may be assayed by any method and examples thereof include an electrical method using an oxygen electrode, and preferably an enzymatic method using peroxidase and an adequate coloring substrate. For example, in the present invention, the assay is preferably carried out in an enzyme manner within a short period of time by a simple procedure. Examples of reagents for assaying hydrogen peroxide by the enzymatic method of the present invention include a reagent comprising 5 to 500 mM, preferably 50 to 100 mM of buffer (pH of 4 to 10 being preferred), 0.01 to 50 mM, preferably 0.1 to 20 mM of 4-aminoantipyrine as a coloring substrate, and 0.1 to 50 U/mL, preferably 1 to 20 U/mL of peroxidase. Buffers used in the present invention include, for example, N-[tris(hydroxymethyl)methyl]glycine, phosphate, acetate, carbonate, tris(hydroxymethyl)-aminomethane, borate, citrate, dimethylglutamate, Tricine, and HEPES. Coloring substrates include, in addition to 4-aminoantipyrine, for example, ADOS (N-ethyl-N-(2-hydroxy-3-sulfopropyl)-m-anisidine), ALOS (N-ethyl-N-(2-hydroxy-3-sulfopropyl) aniline), 10-(carboxymethylaminocarbonyl)-3,7-bis (dimethylamino)-phenothiazine (DA-67), and N-(carboxymethylaminocarbonyl)-4,4'-bis (dimethylamino)-diphenylamine (DA-64). If necessary, various additives, for example, surfactants (e.g., Triton X-100, Bridge 35, Tween 80, cholate), reducing agents (e.g., dithiothreitol, mercaptoethanol, and L-cysteine), bovine serum albumin, and saccharides (e.g., glycerin, lactose, and sucrose), may be appropriately added to a solubilizing agents, stabilizers or the like within a range which does not impair the object of the present invention.

In general, the step of producing hydrogen peroxide by the reaction of the oxidase is preferably carried out concurrently with the assay of hydrogen peroxide. In the present invention, therefore, the oxidase of the present invention is preferably added to the reagents for assaying the hydrogen peroxide in an amount of, for example, 0.1 to 50 U/mL, preferably 1 to 10 U/mL. These reagents for assaying may be used in a dried or dissolved state. Alternatively, the reagents may be used after being impregnated into a carrier in a thin film form, such as an impregnable paper sheet. The enzymes used in the assay reagent of the present invention can be repetitiously used by immobilization in accordance with a conventional method. The assay temperature is, for example, 20 to 45° C., and a temperature employed in a conventional enzyme reaction can be appropriately selected. The time required for the assay can be appropriately selected depending on various assay conditions and, for example, is preferably 0.1 to 60 minutes, particularly preferably 1 to 10 minutes, in the present invention. The level of color development of the assay reagent (change in absorbance) is measured with a spectrophotometer, and the measured value is compared with a standard absorbance, thereby assaying a glycated peptide or glycated protein contained in a sample. A conventional autoanalyzer can be used in the assay.

An assay reagent kit for assaying a glycated protein in a sample according to the present invention comprises protease used for liberating a glycated peptide from the glycated protein, the oxidase of the present invention, a reagent for assaying hydrogen peroxide, and the like. Specific formulations of the respective components can be as described above. The above components may be separately stored and used or the oxidase of the present invention and the reagent for assaying hydrogen peroxide may be stored and used in combination. In the present invention, when a glycated protein is assayed using the reagent kit, for example, a step of liberating a glycated peptide and a step of assaying the liberated glycated peptide may be separately performed in two steps, or alternatively, those components may be combined to perform the above steps consecutively in one step.

Next, a method for assaying a liberated glycated peptide by HPLC will be described. A protease treatment mixture liquid containing a liberated glycated peptide is used in that state for the assay by HPLC. Alternatively, the mixture is optionally filtrated by centrifugation or through membrane and the filtrate is appropriately concentrated or diluted for the assay by HPLC. Any HPLC may be used for the HPLC in the present invention so long as the HPLC can assay the glycated peptide. For example, columns for reversed phase HPLC usable herein include CAPCEL-PAK C-18 (Shiseido Co., Ltd.), TSKgel ODS80Ts (Tosoh Corp.), and Shodex RSpak RP18-415 (Showa Denko K.K.) and columns for ion-exchange HPLC include TSKgel SP-2SW and TSKgel CM-2SW (Tosoh Corp.). After protease treatment, reaction mixture is adsorbed on these columns, and an eluent is used to elute a subject glycated peptide. Any eluent may be used so long as it is suitable for the assay in the present invention, and examples thereof include, in the case of reversed phase column, a mixed solution of acetonitrile and water containing trifluoroacetic acid, a mixed solution of a phosphate buffer and acetonitrile, and a mixed solution of an aqueous solution of ammonia and acetonitrile, and in the case of ion-exchange columns, a mixed solution of a phosphate buffer and a NaCl solution and a mixed solution of an acetate buffer and acetonitrile. Stepwise elution or gradient elution may be carried out using these eluents. Preferable eluents include, for example, a gradient eluent of 0.1% TFA (trifluoroacetic acid)/water-0.1% TFA/30% acetonitrile. Preferably, in the present invention, a column, an eluent, the elution conditions (e.g., elution method, flow rate of an eluent, and temperature) and the like are appropriately combined and the conditions are set up so that the elution peak of the subject α-glycated peptide is separated satisfactorily from that of other components at an optimal level.

As a method for detecting a glycated peptide eluted by an eluent, any method can be utilized as long as the glycated peptide can be detected therewith. For example, usable methods include a method for detecting absorbance at a wavelength of 210 nm, 215 nm, or the like, a method for determining the peak of the subject molecular weight by fractionating each detected peak, followed by mass spectrometry, a method utilizing thin-layer chromatography, and a method in which an elution fraction that was fractionated over time is subjected to colorimetric measurement with ninhydrin or saccharide coloring. As one example, when a method for detecting absorbance is employed, the area of the elution peak of the glycated peptide detected by a monitoring is calculated and the calculated value is compared with the area of the elution peak of a standard substance. Thus, the amount of the glycated peptide and the glycated protein can be assayed.

The present invention will be described in more detail with reference to a reference example and examples, although the technical scope of the present invention is not limited to these examples only.

Reference Example (Production of Glycated Dipeptide)

The α-glycated dipeptide used in the present invention was produced in accordance with the following method. 7.0 g (27.6 mmol) of commercially available dipeptide (valyl histidine (Val-His), BACHEM, Switzerland) was dissolved in 14 mL of water, 5.8 mL of acetic acid was added and dissolved at about 50° C., and the mixture was clarified. Subsequently, 120 mL of ethanol was added thereto and mixed, 14 g (77.8 mmol) of glucose was then added, and the mixture was thoroughly mixed. Thereafter, the mixture was heated in a hermetically sealed container at 80° C. for 6 hours while sporadically stirring. The reaction solution was browned over time. An aliquot was taken from the reaction solution over time, adequately diluted, and subjected to analysis by reversed phase high performance liquid chromatography, thin-layer chromatography, or mass spectrometry to assay the production of the subject glycated dipeptide. In general, a glycated dipeptide can be obtained in a high yield by heating for 6 to 10 hours. Next, the reaction solution was collected and concentrated to fifteen-fold to thirty-fold using a rotary evaporator. The concentrate was adsorbed on a silica gel column (bed volume: 2,000 mL) that had been was equilibrated with 99.5% ethanol and washed with 2 bed volumes of 99.5% ethanol, and impurities such as unreacted glucose were removed. Subsequently, elution was carried out using 3 bed volumes of 95% ethanol, 3 bed volumes of 90% ethanol, 3 bed volumes of 85% ethanol, and 3 bed volumes of 80% ethanol, in that order. Each elution fraction was analyzed by thin-layer chromatography, reverse phase high performance liquid chromatography and the like to collect a 95 to 90% ethanol elution fractions containing a subject fructosyl Val-His. The collected fractions were concentrated to dryness using a rotary evaporator to obtain about 3 g of partially purified product. As a result of mass spectrometry analysis, the molecular weight of the purified product was 416, which was congruous with the molecular weight of fructosyl Val-His, and the structure thereof was confirmed using nuclear magnetic resonance spectrum analysis. In accordance with the conventional method, this partially purified product was subjected to adsorption and desorption using an ion-exchange resin, thereby enhancing the level of purity for use in subsequent experiments. Further, partially purified products of a glycated tripeptide, a glycated tetrapeptide, and a glycated hexapeptide was respectively obtained using a tripeptide, a tetrapeptide, and a hexapeptide, respectively, in the same manner as described above.

EXAMPLE 1

Liberating Glycated Dipeptide from Glycated Hexapeptide

Treating glycated hemoglobin (HbAlc) with endoproteinase Glu-C results in liberation of an α-glycated hexapeptide derived from the β subunit of glycated hemoglobin (HbAlc) (fructosyl Val-His-Leu-Thr-Pro-Glu) (Clin. Chem., 43, 1994–1951 (1997)). Therefore, the following experiment was carried out using fructosyl Val-His-Leu-Thr-Pro-Glu (PEPTIDE INSTITUTE, INC.), which is identical to the α-glycated hexapeptide.

The α-glycated hexapeptide (PEPTIDE INSTITUTE, INC.) was dissolved in water to prepare a 5 mM solution. To 0.1 mL of this solution were added the following combinations of 0.01 mL of protease solution (20 mg/mL) and 0.09 mL of buffer (0.1 M) ((a) to (d)), followed by mixing to subject to protease treatment.

(a) Carboxypeptidase Y (Oriented Yeast), a phosphate buffer (pH 6.5).

(b) AO protease (commercially available from Seishin Corporation), a citric acid-sodium phosphate buffer (pH 6.0).

(c) Peptidase (commercially available from Seishin Corporation), a citric acid-disodium phosphate buffer (pH 6.0).

(d) Molsin (commercially available from Seishin Corporation), a citric acid-disodium phosphate buffer (pH 3.0).

The above mixture was subjected to reaction at 37° C. for 60 minutes. Thereafter, the reaction mixture was suitably concentrated or diluted respectively and assayed by HPLC. CPCEL-PAK C-18 (Shiseido) was used for HPLC (reversed phase high performance liquid chromatography). Gradient elution was carried out using, as an eluent, 0.1% TFA (trifluoroacetic acid)/water-0.1% TFA/30% acetonitrile. An α-glycated dipeptide (fructosyl Val-His) was used as a standard substance. Further, the eluted glycated peptide was analyzed using thin-layer chromatography (a silica plate (Merck) was used, a developing solvent was n-butanol:acetic acid:water=2:1:1, ninhydrin and ethanol-sulfuric acid were used for spot detection). As a result, in each combination of (a), (b), (c), and (d), the α-glycated dipeptide (fructosyl Val-His) was liberated in the protease treatment reaction mixture. Further, each reaction mixture was subjected to amino acid analysis (amino acid analyzer L-8800, Hitashi) and mass spectrometry analysis (mass spectrometer Model M-80B, Hitachi). As a result of identification of the liberated amino acid residue and the measurement of the molecular weight thereof, it was found that, in each case, the α-glycated hexapeptide (fructosyl Val-His-Leu-Thr-Pro-Glu) was cleaved in order from its carboxy terminus and/or internally cleaved and thereby decomposed into a shorter α-glycated peptide. In the case of (a), while the liberation of Glu, Pro, Thr, and Leu residues from the carboxyl terminus was confirmed, the liberation of His residue was not confirmed. This indicates that it was shortened to fructosyl Val-His. Further, the analysis of the reaction mixture by mass spectrometry revealed that a major portion of the glycated peptide which was confirmed after treatment was fructosyl Val-His, and signals with molecular weights corresponding to fructosyl Val-His-Leu and fructosyl Val-His-Leu-Thr were found only at an insignificant level. In (b) and (c), a signal of fructosyl Val-His and a signal of a minor amount of fructosyl Val-His-Leu were found. In (d), only the signal of fructosyl Val-His was found.

EXAMPLE 2

Liberating Glycated Dipeptide from Glycated Protein

Distilled water was added to a glycated hemoglobin (HbAlc) control (International Reagents) to prepare a solution of 8 g/dL (HbAlc contact of about 10%). To 0.05 mL of this solution were added 0.01 mL of protease derived from the genus *Aspergillus* (Molsin, 20 mg/mL) and 0.04 mL of buffer (0.1 M, citric acid-disodium phosphate buffer, pH 3.0), followed by mixing. The mixed solution was treated with protease at 37° C. for 180 minutes. Thereafter, the reaction mixture was subjected to centrifugal filtration using Microcon 3 (fraction molecular weight 3,000 Grace Japan K. K.) and the filtrate was diluted and then assayed by HPLC as described in Example 1. The liberation of fructosyl Val-His was confirmed and the glycated dipeptide was determined based on the area of the elution peak. The glycated protein was assayed using the measured value.

EXAMPLE 3

Obtaining the Modified Oxidase of the Present Invention (1) Preparation of template DNA

*Escherichia coli* DH5α, which maintains a plasmid (pFA5) coding for a fructosyl amino acid oxidase genes derived from a bacteria belonging to the genus *Corynebacterium* (FERM BP-6182), was inoculated into 100 mL of LB-amp medium (1% bactotrypton, 0.5% bactoyeast extract, 0.5% sodium chloride, 50 µg/mL ampicillin, pH 7.0), followed by shake culturing at 30° C. for 24 hours to obtain a cultured product. 1.5 mg of pFA5 plasmid DNA was obtained from the cultured product in accordance with the method described in "Molecular Cloning (2nd Edition, 1989)".

(2) Introduction of mutation

30 µg of pFA5 plasmid DNA was dissolved in 100 µL of hydroxylamine solution (0.8 M hydroxylamine hydrochloride/0.1 M phosphate buffer, pH 6.0/1 mM EDTA). The solution was subjected to mutation treatment at 65° C. for 2 hours and ethanol precipitation was performed by a conventional method to collect a precipitate. The precipitate was dissolved in a TE buffer (10 mM tris-hydrochloric acid buffer, pH 7.5/1 M EDTA), and *Escherichia coli* DH5α strain was transformed in accordance with a method of D. M. Morrison (Method in Enzymology, 68, 326–331, 1979) and inoculated into a LB-amp agar medium (1% bactotrypton, 0.5% bactoyeast extract, 0.5% sodium chloride, 50 µg/mL ampicillin, 1.5% (w/v) agarose, pH 7.0) to culture at 30° C. for 24 hours.

(3) Selection of producing microorganism

About 50,000 strains of colonies that were developed after 18 hours of culturing were transferred to Hybond-C which had been immersed in 30 mg/mL Lysozyme solution. On the then hand, Hybond-C that had been immersed in 50 mM fructosyl Val-His, 0.5 mg/mL peroxidase, 1.0 mg/mL 4-aminoantipyrine, 50 mg/mL TOOS, and 100 mM potassium phosphate buffer (pH 8.0) was prepared. The two Hybond-Cs were placed on each other in such a manner that the surfaces having bacterial cells thereon faced inward, and were then reacted at 37° C. for about 30 minutes to 1 hour. Three strains with color development were selected and inoculated into 10 mL of LB-amp medium, and subjected to shake culturing at 30° C. for 24 hours. Thereafter, the culture solutions was fragmented by ultrasound treatment and centrifuged, and then the supernatant was assayed for its glycated peptide oxidase activity in the above-described manner. As a result, activity was detected in one strain. This strain was designated as *Escherichia coli* DH5α (pFP1).

(4) Enzyme Production

The selected *Escherichia coli* DH5α (pFP1) capable of producing the glycated peptide oxidase of the present invention was inoculated into 10 L of LB-amp medium and cultured while stirring with a jar fermenter at a amount of airflow of 1 L/min at a rate of stirring of 600 rpm at 30° C. for 20 hours. The obtained 20 L of culture solution was concentrated to 5 L with the aid of an ultrafilter membrane with an MW of 50,000 (ASAHI KASEI CORP.) and 1 M potassium phosphate buffer (pH 8.0) was added thereto. Thereafter, bacterial cells were fragmented by DYNO-mill. The fragmented solution was centrifuged at 10,000 rpm for 15 minutes. The resultant supernatant was determined as a crude enzyme solution and subjected to purification in the manner described below.

Potassium chloride was added to the crude enzyme solution to bring the solution of 0.15 M and the solution was adsorbed on 2 L of DEAE-Sephacel column, which had been equilibrated by 50 mM potassium phosphate buffer (pH 8.0) containing 0.15 M potassium chloride. After washing with 2 L of the same buffer, elution was performed using a potassium phosphate buffer (a potassium chloride concentration: a linear gradient of 0.15 M to 0.50 M, pH 8.0). The activity of the obtained eluent was assayed based on the method for measuring a titer of the oxidase of the present invention, active fractions were then collected, the obtained enzyme solution was concentrated using an ultrafilter membrane with an MW of 6,000 (ASAHI KASEI CORP.), and dialyzed with 50 mM potassium phosphate buffer (pH 8.0) containing 16% ammonium sulfate. The product was then adsorbed onto a butyl TOYOPEARL column, which had been equilibrated by 50 mM potassium phosphate buffer (pH 8.0) containing 16% ammonium sulfate, washed with the same buffer, and eluted with 50 mM potassium phosphate buffer (an ammonium sulfate concentration: a linear gradient of 16% to 0%, pH 8.0) to collect active fractions. Subsequently, the enzyme solution was concentrated using an ultrafilter membrane with an MW of 6,000 (ASAHI KASEI CORP.) and dialyzed with 50 mM potassium phosphate buffer (pH 8.0). Thus, the subject enzyme solution was obtained.

EXAMPLE 4

Assay of α-Glycated Dipeptide Using Oxidase

The following reagents were prepared for use in the assay of the glycated dipeptide.

| Reagent A (coloring reagent) | |
|---|---|
| 4-Aminoantipyrine (TOKYO KASEI KOGYO CO., LTD.) | 0.2 mM |
| TOOS | 0.2 mM |
| Peroxidase (Toyobo Co.) | 14.3 U/mL |
| Potassium phosphate buffer (pH 8.0) | 0.1 M |
| Reagent B (oxidase reagent) | |
| Oxidase obtained in Example 3 | 4 U/mL |
| Potassium phosphate buffer (pH 8.0) | 0.02 M |

The α-glycated dipeptide, fructosyl Val-His obtained in accordance with the method described in Reference Example were used to prepare a 1.0 mmol/L solution. This solution was diluted and glycated dipeptide-containing samples with various concentrations (25, 50, 75, and 100 μmol/L) were prepared. 2.1 mL of Reagent A was added to each of the glycated dipeptide-containing samples of 0.3 mL, and the samples were heated at 37° C. for 5 minutes. 0.6 mL of Reagent B was added to each heated solution and the solution was reacted at 37° C. for 10 minutes. The absorbance at 555 nm was measured and an increase in absorbance (ΔOD) after 10 minutes of reaction was determined. An example of the measurement result of α-glycated dipeptides with various concentrations is shown in FIG. 1. FIG. 1 shows a linear correlation between ΔOD and the α-glycated dipeptide concentration. The α-glycated dipeptide in a sample can be assayed in a short period of time with high accuracy. In contrast, instead of the oxidase of the present invention in Reagent B (oxidase reagent), 4 U/mL of the fructosyl amino acid oxidase (Japanese Patent Publication (kokoku) Nos. 33997/1993 (Hei5-33997) and 65300/1994 (Hei6-65300)) produced from a bacteria belonging to the conventional genus *Corynebacterium* was used to assay in the same manner as described above. None of the samples, however, exhibit the increase in adsorbance (ΔD). This indicates that modification of the conventional fructosyl amino acid oxidase has led to the provision of a novel oxidase of the present invention having activity that acts on a glycated peptide.

EXAMPLE 5

Assay of Glycated Protein Using Oxidase

The following reagents were prepared for use in the assay of the glycated protein using the oxidase of the present invention.

Reagent A (coloring reagent)
Same as Example 4

| Reagent B (oxidase reagent) | |
|---|---|
| Same as Example 4. | |
| Reagent C (protease reagent) | |
| Molsin (commercially available from Selshin Corporation) | 20 mg/mL |
| Potassium chloride-hydrochloric acid buffer (pH 3.0) | 100 mM |

Figure 2:
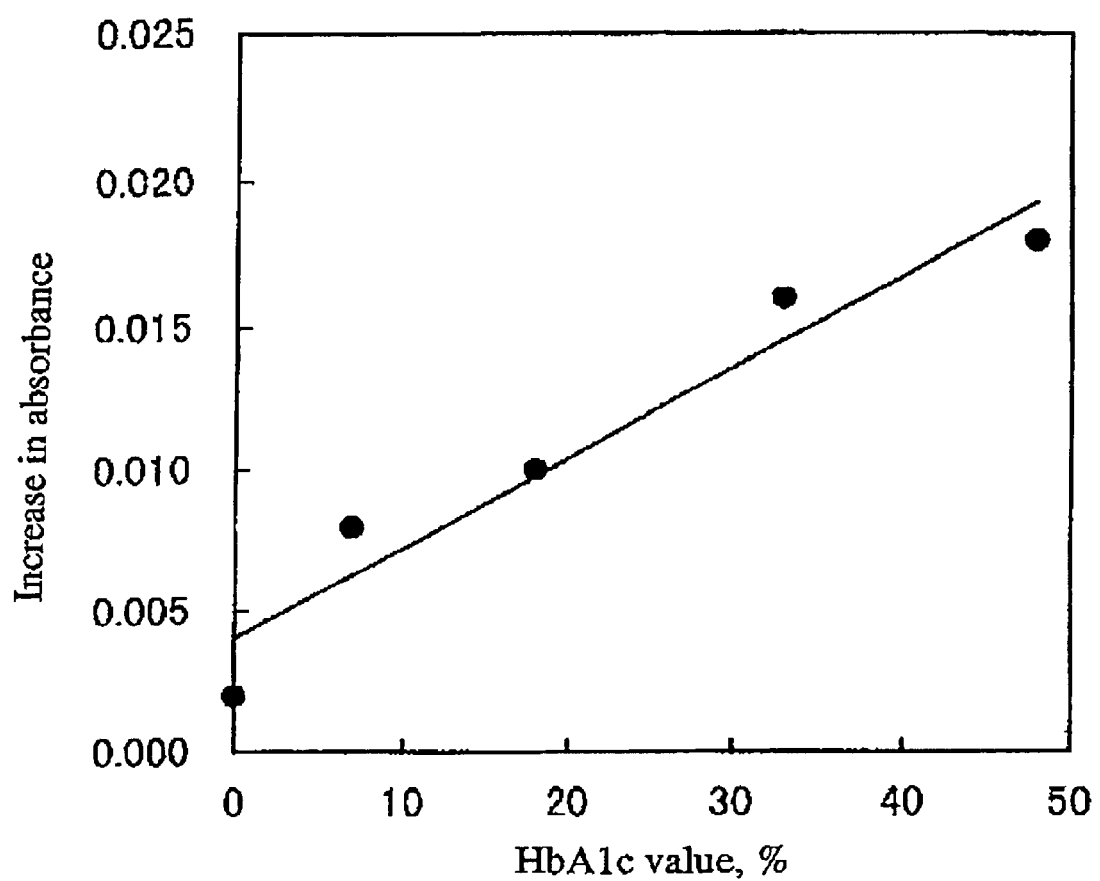
FIG. 2 shows a result of assay of glycated hemoglobin (HbAlc) in a sample using the method of the present invention.

A nonglycated hemoglobin fraction and a glycated hemoglobin (HbAlc) fraction which were fractionated from human hemolysate in accordance with conventional methods (a combination of centrifugation, concentrating dialysis, ion exchange high performance liquid chromatography and the like) were mixed in a suitable ratio to prepare several types of samples with a HbAlc content (HbAlc value) of 0 to 50% based on the entire hemoglobin. 100 μL of Reagent C (protease reagent) was added to 100 μL of the sample and the sample was treated with protease at 37° C. for 1 hour. The reaction mixture was then boiled to stop protease reaction. Subsequently, 0.5 M NaOH was added to the reaction mixture to adjust the pH value to 7, followed by centrifugation (12,000 rpm, 5 minutes) to fractionate the supernatant. 2.1 mL of Reagent A (coloring reagent) and 0.6 mL of Reagent B (oxidase reagent) were added to 0.3 mL of this supernatant, followed by mixing. The mixture was then subjected to reaction at 37° C. for 30 minutes. The absorbance at 555 nm before the initiation of the reaction and the absorbance at 555 nm after the completion of the reaction were respectively measured to determine the increase in the absorbance (ΔOD). An example of the measurement result for several samples with different HbAlc values is shown in FIG. 2. This result shows a linear correlation between ΔOD and the amount of HbAlc in the starting sample. Thus, glycated hemoglobin in a sample can be assayed in a simple and rapid manner with high accuracy.

INDUSTRIAL APPLICABILITY

The assay method of the present invention is effectively used in diagnosis or control of diabetic conditions by realizing the assay of a glycated protein, for example, glycated hemoglobin, in a short period of time, in a simple manner, and with high accuracy.

All publications, parents and patent applications cited herein are incorporated herein by reference in their entirety.

What is claimed is:

1. A method for assaying the presence and/or amount of an alpha glycated peptide in a sample comprising:
    treating a sample suspected of containing an α-glycated peptide with at least one oxidase which produces hydrogen peroxide upon reacting with the α-glycated peptide, and
    determining the presence and/or amount of a generated product or consumed substance by said reaction.

2. The method of claim 1, comprising determining the presence and/or amount of hydrogen peroxide generated by treatment of the sample suspected of containing an α-glycated peptide with said at least one oxidase.

3. The method of claim 2, wherein the present and/or amount of hydrogen peroxide generated by treatment of the sample suspected of containing an α-glycated peptide with said at least one oxidase is determined using an oxygen electrode.

4. The method of claim 2, wherein the presence and/or amount of hydrogen peroxide generated by treatment of the sample suspected of containing an α-glycated peptide with said at least one oxidase is determined enzymatically.

5. The method of claim 1, wherein said at least one oxidase is derived from a modified *Corynebacterium* amino acid oxidase gene.

6. The method of claim 1, wherein said at least one oxidase is the same as that produced by *Escherichia coli* DH5α(pFP1).

7. The method of claim 1, wherein said glycated peptide is an α-glycated dipeptide.

8. The method of claim 1, wherein a peptide portion of the α-glycated peptide is a short chain peptide having 2 to 6 amino acids.

9. The method of claim 1, wherein the α-glycated peptide is fructosyl valyl histidine.

10. The method of claim 1, further comprising treating a sample suspected of containing a glycated protein with at least one protease for a time and under conditions suitable for the production of an α-glycated peptide to obtain said sample suspected of containing an α-glycated peptide.

11. The method of claim 10, wherein said at least one protease is derived from *Aspergillus*.

12. The method of claim 10, wherein said at least one protease is derived from the genus *Aspergillus* and is selected from the group consisting of Molsin, AO Protease and Peptidase.

13. The method of claim 10, wherein said at least one protease is derived from *Saccharomyces*.

14. The method of claim 10, wherein said at least one protease is carboxypeptidase Y.

15. The method of claim 10, wherein said at least one protease is derived from *Bacillus*.

16. The method of claim 10, wherein said at least one protease is Protin P.

17. The method of claim 10, wherein said sample suspected of containing a glycated protein is suspected of containing HbAlc.

18. The method of claim 10, wherein said sample suspected of containing a glycated protein is suspected of containing a glycated protein other than HbAlc.

19. The method of claim 10, wherein said sample is obtained from a subject suspected of having a diabetic condition or who has a diabetic condition.

20. The method of claim 10, wherein said sample is obtained from a subject who does not have a diabetic condition.

21. A method for assaying the presence and/or amount of a glycated protein in a sample comprising:
    treating a sample suspected of containing a glycated protein with at least one protease and
    determining the presence or absence of, and/or amount of, fructosyl valyl histidine liberated from said sample.

22. The method of claim 21, wherein the presence or absence of, or the amount of, fructosyl valyl histidine liberated from said sample is determined by HPLC.

23. A kit comprising:
    an oxidase which produces hydrogen peroxide by reacting with an α-glycated peptide.

24. The kit of claim 23, wherein said oxidase is an oxidase derived from a modified *Corynebacterium* fructosyl amino acid oxidase gene.

25. The kit of claim 23, wherein said oxidase is the same as that produced by *Escherichia coli* DH5α(pFP1).

26. The kit of claim 23, further comprising one or more protease(s).

27. The kit of claim 23, further comprising at least one reagent for assaying hydrogen peroxide.

28. The kit of claim 23, further comprising a nonglycated hemoglobin fraction and/or a glycated hemoglobin (HbAlc) fraction.

* * * * *